US006135983A

United States Patent [19]

Andrews et al.

[11] Patent Number: 6,135,983

[45] Date of Patent: Oct. 24, 2000

[54] GASTRIC-TUBE FEEDING SYSTEM

[76] Inventors: Leonard Lee Andrews, 4817 E. Michigan, Freno, Calif. 93703; Daniel H. Hanson, 2600 E. Sierra, Fresno, Calif. 93710

[21] Appl. No.: 09/397,341

[22] Filed: Sep. 15, 1999

[51] Int. Cl.[7] .................. A61M 5/00

[52] U.S. Cl. .................. 604/257

[58] Field of Search .................. 604/27, 30, 246–254, 604/79, 257, 261, 275; 248/125, 159, 215; D24/127–129

[56] References Cited

U.S. PATENT DOCUMENTS

| | | | |
|---|---|---|---|
| D. 373,823 | 9/1996 | Baldwin | D24/128 |
| 4,042,232 | 8/1977 | Lile et al. | 269/328 |
| 4,176,349 | 11/1979 | Fliegel | 340/613 |
| 4,425,123 | 1/1984 | Di Salvo | 604/247 |
| 4,455,139 | 6/1984 | Gordon et al. | 604/247 |
| 4,744,536 | 5/1988 | Banclaari | 248/125 |
| 4,769,015 | 9/1988 | Bloxom, Jr. | 604/277 |

*Primary Examiner*—Sharon Kennedy
*Assistant Examiner*—Deborah Blyveis
*Attorney, Agent, or Firm*—Robert Charles Hill

[57] ABSTRACT

A gastric-tube feeding system comprises a table-top stand with a loop that holds a feeding syringe aloft at an adjustable elevation. A funnel is used to simplify the filling of the feeding syringe with liquid food diet from a can.

3 Claims, 1 Drawing Sheet

GASTRIC-TUBE FEEDING SYSTEM

BACKGROUND OF THE INVENTION

1. Field of the Invention

The present invention relates to medical out-patient devices, and more particularly to feeding systems for people who have had gastric feeding tubes surgically implanted.

2. Description of Related Art

Cancer of the esophagus used to always be fatal. But now with surgical removal of the cancerous esophagus and chemotherapy, many people are now surviving. Once the esophagus has been removed, a gastric feeding tube is surgically implanted so that the patients can continue to feed themselves at home.

It has been estimated that as many as 74,000 Americans have a gastric feeding tube inserted each year. A diet of liquid food is taken through a large detachable syringe and extension tubing. The patient is expected in prior art devices to hold the syringe in one hand and pour the food into the rather small mouth of the syringe with the other hand. This challenge is often too much for patients that are weak, feeble, suffer from tremors, or who are just clumsy. Diarrhea is a side effect of chemotherapy and patients often have just a few moments to proceed to the bathroom. The result is often an embarrassing mess of food and a need for recurring assistance. A funnel can help, but still the whole is difficult to use.

An intravenous (IV) bag and pole are one solution. But the IV bag needs opening and closing, food cannot be poured in easily, and the IV pole is inconvenient and often too high.

An intestinal irrigation apparatus that could be adapted for gastric tube feeding is described in U.S. Pat. No. 4,769,015, issued Sep. 6, 1988, to Ingrid B. Bloxom, Jr. In particular, a table top version is described that holds a douche or enema bag aloft on a hook. But such device is not adjustable and incompatible with a feeding tube syringe.

A gastrointestinal tube syringe holder is illustrated in United States Design Patent, D.373,823, issued Sep. 17, 1996, to Donald M. Baldwin. Such shows a syringe holder with a clamp, that evidently is supposed to fit on the edge of a table. This device too is not adjustable, and it must be used on a table or desk where an edge is not available for the clamp to bite on. It cannot be used on a flat surface like a table top. The elevation of the feeding syringe is predetermined by the manufacturer.

SUMMARY OF THE INVENTION

An object of the present invention is to provide a gastric-tube feeding system that is effective and easy to use.

Another object of the present invention is to provide a gastric-tube feeding system that allows the users to feed themselves.

Briefly, a gastric-tube feeding system embodiment of the present invention comprises a table-top stand with a loop that holds a feeding syringe aloft at an adjustable elevation. A funnel is used to simplify the filling of the feeding syringe with liquid food diet from a can.

An advantage of the present invention is that a gastric-tube feeding system is provided that is simple and easy enough for an out-patient to use themselves.

Another advantage of the present invention is that a gastric-tube feeding system is provided that is convenient and portable.

A still further advantage of the present invention is that a gastric-tube feeding system is provided that is inexpensive to manufacture, thus would be available at a minimal cost to a large number of patients.

The above and still further objects, features, and advantages of the present invention will become apparent upon consideration of the following detailed description of specific embodiments thereof, especially when taken in conjunction with the accompanying drawings.

DETAILED DESCRIPTION OF THE INVENTION

Figure 1:
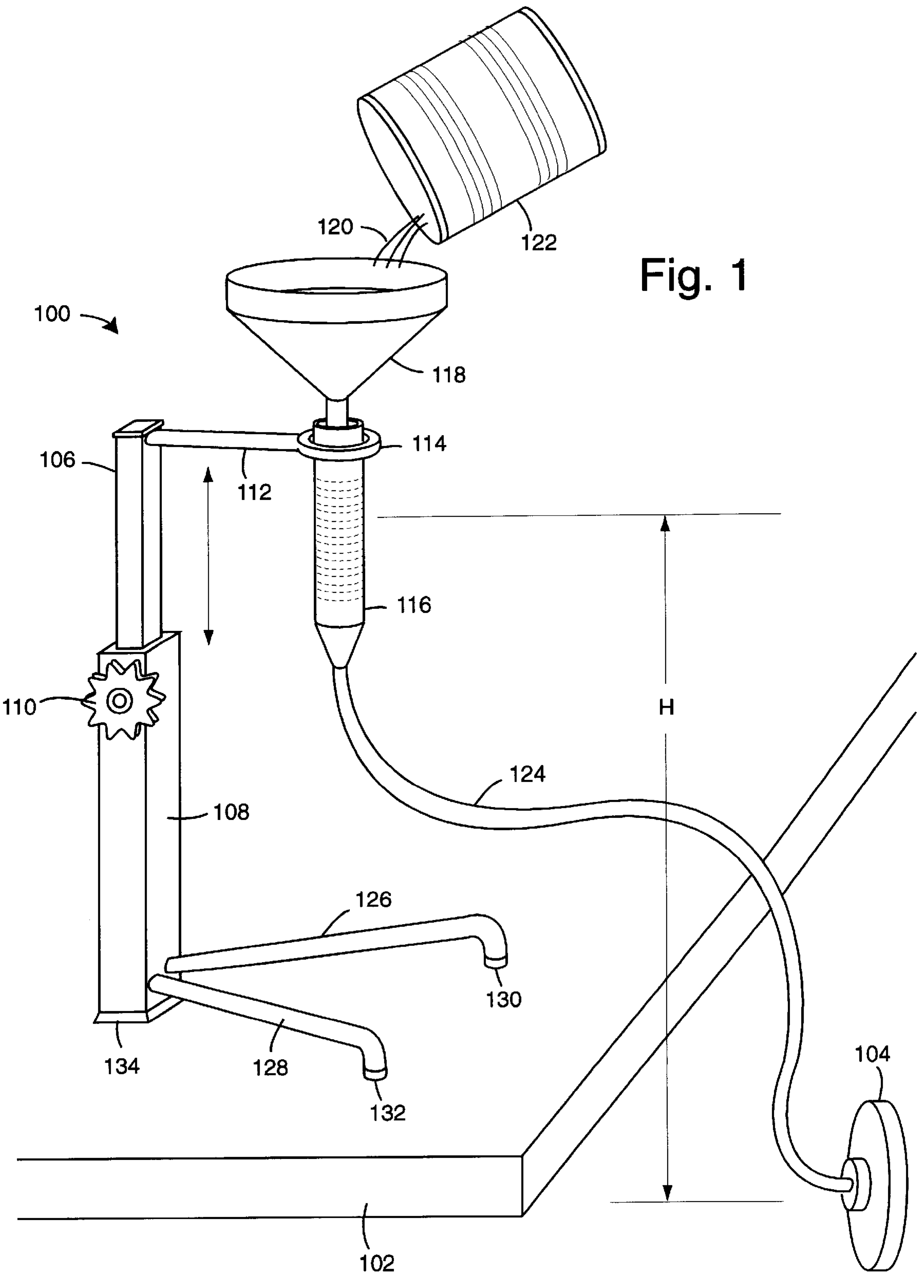
FIG. 1 is a diagram of a gastric-tube feeding system embodiment of the present invention.

FIG. 1 illustrates a gastric-tube feeding system embodiment of the present invention referred to herein by the reference numeral 100. The gastric-tube feeding system 100 preferably sits on a table 102 during use. A feeding valve 104 represents one that has been surgically implanted in the abdominal wall of an out-patient, e.g., one who has suffered a surgical removal of a cancerous esophagus.

The gastric-tube feeding system 100 includes an upper mast 106 that can be adjusted up and down inside a lower mast 108 and locked with an adjustment knob 110. A boom 112 supports a ring 114 into which is placed a feeding syringe 116. The ring 114 has a small opening to accommodate the intravenous (IV) bag. A funnel 118 is used to make pouring a liquid food diet 120 from a can 122 easier. A surgical tubing 124 connects to the feeding valve 104. The surgical tubing 124 is permanently attached to the feeding valve 104. A cap is put over the end of the surgical tubing 124 to prevent leakage of the stomach. A pair of stabilizing legs 126 and 128 are each equipped with a rubber foot 130 and 132. Another rubber foot 134 at the bottom of the lower mast 108 helps prevent slipping of the gastric-tube feeding system 100 on the table 102. A rubber cap seals the top of the upper mast 106.

The user preferably sits on a chair at the table 102 while using the gastric-tube feeding system 100. The elevation of the feeding syringe 116 is preferably adjusted to a height "H" that allows a free-flow of liquid food diet 120 to flow into the feeding valve 104 and into the out-patient's stomach. After feeding, water is poured into the feeding syringe 116 and through the surgical tubing 124 and feeding valve 104. The syringe 116 and funnel 118 are washed and cleaned.

Although particular embodiments of the present invention have been described and illustrated, such is not intended to limit the invention. Modifications and changes will no doubt become apparent to those skilled in the art, and it is intended that the invention only be limited by the scope of the appended claims.

The invention claimed is:

1. A gastric-tube feeding system, comprising:

an adjustable extension mast;

a set of stabilizing legs attached to the bottom of the adjustable extension mast;

an adjustment knob connected to lock the adjustable extension mast at a variety of heights;

a boom attached at one end to an upper portion of the adjustable extension mast;

a syringe holder attached to a distal end of the boom;

a feeding syringe disposed within said syringe holder; and a funnel in said feeding syringe;

wherein, a user with a surgically implanted gastric feeding valve places the feeding system on a table top and fills a feeding syringe with liquid diet food, and a connecting tube between said gastric feeding valve and said feeding syringe delivers said liquid diet food to the stomach of said user.

2. The gastric-tube feeding system of claim 1, wherein:

said funnel inserted into the top of the feeding syringe provides a wide receiving area to guide a liquid diet food poured from a can into the feeding syringe.

3. The gastric-tube feeding system of claim 2, wherein:

said liquid diet food flows by force of gravity alone from the feeding syringe through a connecting tube into said user's stomach.

* * * * *